United States Patent
Heath et al.

(10) Patent No.: US 7,348,143 B2
(45) Date of Patent: Mar. 25, 2008

(54) METHOD OF VISUALIZING NON-TARGETED METABOLOMIC DATA GENERATED FROM FOURIER TRANSFORM ION CYCLOTRON RESONANCE MASS SPECTROMETERS

(75) Inventors: Douglas Heath, Saskatoon (CA); Dayan Goodenowe, Saskatoon (CA)

(73) Assignee: Phenmenome Discoveries Inc., Saskatchewan (CA)

( * ) Notice: Subject to any disclaimer, the term of this patent is extended or adjusted under 35 U.S.C. 154(b) by 420 days.

(21) Appl. No.: 10/508,179

(22) PCT Filed: Mar. 20, 2003

(86) PCT No.: PCT/CA03/00389

§ 371 (c)(1),
(2), (4) Date: Dec. 14, 2004

(87) PCT Pub. No.: WO03/081506

PCT Pub. Date: Oct. 2, 2003

(65) Prior Publication Data

US 2005/0107957 A1 May 19, 2005

(30) Foreign Application Priority Data

Mar. 22, 2002 (US) ............................... 60/366,277

(51) Int. Cl.
*C12Q 1/68* (2006.01)
(52) U.S. Cl. ........................................... 435/6; 435/7.1
(58) Field of Classification Search ............... 435/6, 435/29; 324/309, 307
See application file for complete search history.

(56) References Cited

U.S. PATENT DOCUMENTS 4,956,788 A 9/1990 Guan et al.

(Continued)

FOREIGN PATENT DOCUMENTS

CA 2092570 A1 9/1991

(Continued)

OTHER PUBLICATIONS

Jorg Darius, "On-column gas chromatographic-mass spectrometric assay for metabolic profiling of valproate in brain tissue and serum," Journal of Chromatography B: Biochemical Applications, vol. 682, 1996, pp. 67-72.

(Continued)

*Primary Examiner*—Robert Kim
*Assistant Examiner*—Johnnie L Smith, II
(74) *Attorney, Agent, or Firm*—Rothwell, Figg, Ernst & Manbeck p.c.

(57) ABSTRACT

The invention can be summarized as follows. The present invention provides a method of displaying spectroscopic data comprising in steps of, i) obtaining spectroscopic data from a plurality of samples, each sample comprising one or more components wherein each component is characterized by an ordered pair (X,Y) of data comprising data element value X and data element value Y, wherein X is a data element value, equivalent or directly proportional to the mass of the component, and Y is a data element value equivalent or directly proportional to the amount of the component; ii) identifying all unique components comprising a common data element value X in said samples; computing the average of all X therefrom; and determining the average and optionally, the standard deviation for all Y values from all ordered data pairs comprising a common X; iii) generating a data structure comprising an array of codable cells, each cell assigned a color or other identifiable characteristic based on the relationship of the amount of each unique component present in each of said samples in relation to a predetermined value or other characteristic of the spectroscopic data. Also disclosed are data structures comprising spectroscopic data.

61 Claims, 6 Drawing Sheets

U.S. PATENT DOCUMENTS

| | | | |
|---|---|---|---|
| 4,978,852 | A | 12/1990 | Williams et al. |
| 5,233,190 | A | 8/1993 | Schlereth et al. |
| 5,636,350 | A | 6/1997 | Eick et al. |
| 6,680,203 | B2 | 1/2004 | Dasseux et al. |
| 6,873,914 | B2* | 3/2005 | Winfield et al. ............ 702/19 |
| 2002/0042075 | A1* | 4/2002 | Nelson .................... 435/6 |
| 2003/0113761 | A1* | 6/2003 | Tan et al. ................. 435/6 |
| 2004/0029120 | A1* | 2/2004 | Goodenowe ............... 435/6 |
| 2004/0143461 | A1* | 7/2004 | Watkins .................... 705/2 |
| 2005/0170372 | A1* | 8/2005 | Afeyan et al. ............. 435/6 |
| 2006/0228730 | A1* | 10/2006 | Rando et al. .............. 435/6 |

FOREIGN PATENT DOCUMENTS

| | | |
|---|---|---|
| CA | 2185574 | 9/1995 |
| CA | 2252715 | 11/1997 |
| CA | 2264535 | 3/1998 |
| CA | 2339817 | 2/2000 |
| CA | 2 360 816 | 10/2000 |
| CA | 2303758 | 10/2000 |
| CA | 2303761 | 10/2000 |
| EP | 1 182 615 A1 | 2/2002 |
| WO | WO 00/77712 A1 | 12/2000 |
| WO | 0138568 A2 | 5/2001 |
| WO | WO 01/57518 A2 | 8/2001 |
| WO | WO 02/04957 A2 | 1/2002 |
| WO | WO 03/005628 A2 | 1/2003 |

OTHER PUBLICATIONS

Toshihiro Shinka, "Urine screening of five-day-old newborns: metabolic profiling of neonatal galactosuria," Journal of Chromatography B, vol. 732, 1999, pp. 469-477.

Richard N. Trethewey, "Commentary Metabolic profiling: A Rosetta Stone for genomics?," Plant Biology, vol. 2, 1999, pp. 83-85.

Asaph Aharoni, et al., "Nontargeted Metabolome Analysis by Use of Fourier Transform Ion Cyclotron Mass Spectrometry", A Journal of Integrative Biology, vol. 6, No. 3, 2002, pp. 217-234.

Willam A. Feeney, "Gray Scale Diagrams as Business Charts", IEEE, 1991, pp. 140-147.

Markus Muller, et al., "Visualization and Analysis of Molecular Scanner Peptide Mass Spectra", American Society of Mass Spectrometry, vol. 13, 2002, pp. 221-231.

* cited by examiner

Figure 1: Metex Sample File #170

| nMass | Intensity | NE | Emperical Formula #1 | Err | Emperical Formula #2 | Err | Emperical Formula #3 | Err | Emperical Formula #4 | Err |
|---|---|---|---|---|---|---|---|---|---|---|
| 300.057819 | 7.19E+06 | 2 | C8 H4 N12 O2 P0 S0 | 0.66 | C8 H12 N8 O1 P0 S2 | 0.90 | | | | |
| 300.205935 | 6.84E+06 | 1 | C16 H24 N6 O0 P0 S0 | 1.03 | | | | | | |
| 326.072251 | 1.33E+07 | 4 | C9 H10 N8 O6 P0 S0 | 0.24 | C17 H14 N2 O3 P0 S1 | 0.80 | C9 H18 N4 O5 P0 S2 | 1.19 | C10 H22 N4 O0 P0 S4 | 1.46 |
| 356.006014 | 8.48E+06 | 2 | C11 H8 N4 O8 P0 S1 | 0.76 | C1 H0 N20 O0 P0 S2 | 1.10 | | | | |
| 367.345288 | 1.41E+07 | 1 | C23 H45 N1 O2 P0 S0 | 0.70 | | | | | | |
| 374.243371 | 1.64E+07 | 1 | C19 H30 N6 O2 P0 S0 | 0.92 | | | | | | |
| 378.144474 | 6.39E+06 | 3 | C12 H26 N8 O0 P0 S3 | 0.58 | C12 H18 N12 O1 P0 S1 | 0.66 | C19 H18 N6 O3 P0 S0 | 1.15 | | |
| 380.290305 | 5.42E+06 | 1 | C19 H36 N6 O2 P0 S0 | 0.87 | | | | | | |
| 390.142868 | 5.48E+06 | 1 | C19 H22 N2 O7 P0 S0 | 0.43 | | | | | | |
| 392.326316 | 5.22E+06 | 1 | C21 H40 N6 O1 P0 S0 | 0.11 | | | | | | |

Figure 2: Combined Metabolite File From Multiple Biological Samples (#170 to #173)

| Sample # | Code | Mass | Intensity |
|---|---|---|---|
| 170 | 11 | 300.057819 | 7.19E+06 |
| 170 | 11 | 300.205935 | 6.84E+06 |
| 170 | 11 | 326.072251 | 1.33E+07 |
| 170 | 11 | 356.006014 | 6.48E+06 |
| 170 | 11 | 367.345288 | 1.41E+07 |
| 170 | 11 | 374.243371 | 1.64E+07 |
| 170 | 11 | 378.144474 | 6.39E+06 |
| 170 | 11 | 380.290305 | 5.42E+06 |
| 170 | 11 | 390.142868 | 5.48E+06 |
| 170 | 11 | 392.326316 | 5.22E+06 |
| 171 | 11 | 300.20593 | 3.56E+07 |
| 171 | 11 | 326.071958 | 6.27E+06 |
| 171 | 11 | 328.236655 | 6.87E+07 |
| 171 | 11 | 329.138754 | 1.22E+07 |
| 171 | 11 | 356.006023 | 7.70E+06 |
| 171 | 11 | 367.345251 | 2.24E+07 |
| 171 | 11 | 374.243287 | 4.40E+07 |
| 171 | 11 | 378.144179 | 3.05E+07 |
| 171 | 11 | 378.310499 | 9.64E+06 |
| 171 | 11 | 379.147462 | 8.16E+06 |
| 171 | 11 | 380.18893 | 6.04E+06 |
| 171 | 11 | 380.290156 | 2.00E+07 |
| 171 | 11 | 390.144005 | 1.89E+07 |
| 171 | 11 | 390.156881 | 1.34E+07 |
| 171 | 11 | 392.326145 | 2.42E+07 |
| 171 | 11 | 394.13847 | 7.19E+06 |
| 172 | 11 | 300.205883 | 1.43E+07 |
| 172 | 11 | 326.071944 | 1.49E+07 |
| 172 | 11 | 328.236654 | 2.91E+07 |
| 172 | 11 | 356.005902 | 1.06E+07 |
| 172 | 11 | 367.345212 | 2.40E+07 |
| 172 | 11 | 374.243207 | 2.33E+07 |
| 172 | 11 | 378.144138 | 1.06E+07 |
| 172 | 11 | 380.289936 | 8.12E+06 |
| 172 | 11 | 390.143654 | 6.56E+06 |
| 172 | 11 | 392.326346 | 1.20E+07 |
| 173 | 11 | 300.205886 | 3.77E+07 |
| 173 | 11 | 301.139005 | 1.09E+07 |
| 173 | 11 | 328.236605 | 6.96E+07 |
| 173 | 11 | 329.138727 | 8.96E+06 |
| 173 | 11 | 348.134579 | 1.03E+07 |
| 173 | 11 | 348.177108 | 8.42E+06 |
| 173 | 11 | 356.006045 | 1.12E+07 |
| 173 | 11 | 367.345121 | 1.70E+07 |
| 173 | 11 | 374.243195 | 5.11E+07 |
| 173 | 11 | 374.315531 | 5.98E+06 |
| 173 | 11 | 378.144153 | 3.54E+07 |
| 173 | 11 | 378.310641 | 1.95E+07 |
| 173 | 11 | 379.147405 | 8.03E+06 |
| 173 | 11 | 380.188964 | 1.07E+07 |
| 173 | 11 | 380.289997 | 3.67E+07 |
| 173 | 11 | 388.258123 | 6.67E+06 |
| 173 | 11 | 388.33124 | 6.05E+06 |
| 173 | 11 | 390.143731 | 3.34E+07 |
| 173 | 11 | 390.310944 | 5.62E+06 |
| 173 | 11 | 392.289605 | 8.32E+06 |
| 173 | 11 | 392.326058 | 4.70E+07 |
| 173 | 11 | 394.138914 | 7.46E+06 |

Figure 3: Unique Average Mass File Based on Sample Data from Figure 2

| Mean Mass | StdDev Mass | Mean Int | StdDev Int | N | Intensity of 170 | Intensity of 171 | Intensity of 172 | Intensity of 173 |
|---|---|---|---|---|---|---|---|---|
| 300.057819 | 0.00E+00 | 7.188800E+06 | 0.00E+00 | 1 | 7.188800E+06 | | | |
| 300.205909 | 2.73E-05 | 2.359573E+07 | 1.41E+07 | 4 | 1.842900E+06 | 3.555900E+07 | 1.432300E+07 | 3.765800E+07 |
| 301.139005 | 0.00E+00 | 1.092600E+07 | 0.00E+00 | 1 | | | | 1.092600E+07 |
| 326.072051 | 1.54E-04 | 1.147967E+07 | 4.22E+06 | 3 | 1.331500E+07 | 6.265000E+06 | 1.485900E+07 | |
| 328.236638 | 3.01E-05 | 5.578233E+07 | 2.05E+07 | 3 | | 6.869400E+07 | 2.905700E+07 | 6.959600E+07 |
| 329.138741 | 1.65E-05 | 1.059135E+07 | 2.00E+06 | 2 | | 1.222500E+07 | | 8.957700E+06 |
| 348.134579 | 0.00E+00 | 1.028300E+07 | 0.00E+00 | 1 | | | | 1.028300E+07 |
| 348.177108 | 0.00E+00 | 8.421000E+06 | 0.00E+00 | 1 | | | | 8.421000E+06 |
| 356.005996 | 7.27E-05 | 8.992475E+06 | 2.11E+06 | 4 | 6.483500E+06 | 7.700400E+06 | 1.055800E+07 | 1.122800E+07 |
| 367.345218 | 7.88E-05 | 1.936950E+07 | 4.21E+06 | 4 | 1.407000E+07 | 2.244300E+07 | 2.401500E+07 | 1.695000E+07 |
| 374.243265 | 7.89E-05 | 3.368725E+07 | 1.67E+07 | 4 | 1.636700E+07 | 1.395500E+07 | 2.334600E+07 | 5.108100E+07 |
| 374.315531 | 0.00E+00 | 5.983600E+06 | 0.00E+00 | 1 | | | | 5.983600E+06 |
| 378.144236 | 1.47E-04 | 2.072585E+07 | 1.34E+07 | 4 | 6.388400E+06 | 3.053500E+07 | 4.060600E+06 | 3.537400E+07 |
| 378.310570 | 8.70E-05 | 1.458655E+07 | 6.06E+06 | 2 | | 9.635100E+06 | | 1.953800E+07 |
| 379.147434 | 3.49E-05 | 8.096600E+06 | 8.30E+04 | 2 | | 8.164400E+06 | | 8.028800E+06 |
| 380.188947 | 2.08E-05 | 8.381150E+06 | 2.86E+06 | 2 | | 6.043300E+06 | | 1.071900E+07 |
| 380.290099 | 1.65E-04 | 1.756248E+07 | 1.32E+07 | 4 | 5.424400E+06 | 1.997400E+07 | 8.115500E+06 | 3.673600E+07 |
| 388.258123 | 0.00E+00 | 6.673200E+06 | 0.00E+00 | 1 | | | | 6.673200E+06 |
| 388.331240 | 0.00E+00 | 6.048300E+06 | 0.00E+00 | 1 | | | | 6.048300E+06 |
| 390.143565 | 5.48E-04 | 1.609270E+07 | 1.25E+07 | 4 | 5.477000E+06 | 1.892600E+07 | 6.558800E+06 | 3.340900E+07 |
| 390.156881 | 0.00E+00 | 1.335000E+07 | 0.00E+00 | 1 | | 9.335000E+06 | | |
| 390.310944 | 0.00E+00 | 5.616000E+06 | 0.00E+00 | 1 | | | | 5.616000E+06 |
| 392.289605 | 0.00E+00 | 8.319100E+06 | 0.00E+00 | 1 | | | | 8.319100E+06 |
| 392.326216 | 1.43E-04 | 2.210743E+07 | 2.02E+07 | 4 | 5.223700E+06 | 2.418700E+07 | 1.201300E+07 | 4.700600E+07 |
| 394.138692 | 2.72E-04 | 7.325000E+06 | 1.62E+05 | 2 | | 7.192700E+06 | | 7.457300E+06 |

Figure 4: Absolute Intensity of Metabolite Peaks in Each Sample, Represented in Colour

| Mean Mass | StdDev Mass | Mean Int | StdDev Int | N | Int 170 | Int 171 | Int 172 | Int 173 |
|---|---|---|---|---|---|---|---|---|
| 300.057819 | 0.00E+00 | 7.188800E+06 | 0.00E+00 | 1 | | | | |
| 300.205909 | 2.73E-05 | 2.359573E+07 | 1.41E+07 | 4 | | | | |
| 301.139005 | 0.00E+00 | 1.092600E+07 | 0.00E+00 | 1 | | | | |
| 326.072051 | 1.54E-04 | 1.147967E+07 | 4.22E+06 | 3 | | | | |
| 328.236638 | 3.01E-05 | 5.578233E+07 | 2.05E+07 | 3 | | | | |
| 329.138741 | 1.65E-05 | 1.059135E+07 | 2.00E+06 | 2 | | | | |
| 348.134579 | 0.00E+00 | 1.028300E+07 | 0.00E+00 | 1 | | | | |
| 348.177108 | 0.00E+00 | 8.421000E+06 | 0.00E+00 | 1 | | | | |
| 356.005996 | 7.27E-05 | 8.992475E+06 | 2.11E+06 | 4 | | | | |
| 367.345218 | 7.88E-05 | 1.936950E+07 | 4.21E+06 | 4 | | | | |
| 374.243265 | 7.89E-05 | 3.368725E+07 | 1.67E+07 | 4 | | | | |
| 374.315531 | 0.00E+00 | 5.983600E+06 | 0.00E+00 | 1 | | | | |
| 378.144236 | 1.47E-04 | 2.072585E+07 | 1.34E+07 | 4 | | | | |
| 378.310570 | 8.70E-05 | 1.458655E+07 | 6.06E+06 | 2 | | | | |
| 379.147434 | 3.49E-05 | 8.096600E+06 | 8.30E+04 | 2 | | | | |
| 380.188947 | 2.08E-05 | 8.381150E+06 | 2.86E+06 | 2 | | | | |
| 380.290099 | 1.65E-04 | 1.756248E+07 | 1.32E+07 | 4 | | | | |
| 388.258123 | 0.00E+00 | 6.673200E+06 | 0.00E+00 | 1 | | | | |
| 388.331240 | 0.00E+00 | 6.048300E+06 | 0.00E+00 | 1 | | | | |
| 390.143565 | 5.48E-04 | 1.609270E+07 | 1.25E+07 | 4 | | | | |
| 390.156881 | 0.00E+00 | 1.335000E+07 | 0.00E+00 | 1 | | | | |
| 390.310944 | 0.00E+00 | 5.616000E+06 | 0.00E+00 | 1 | | | | |
| 392.289605 | 0.00E+00 | 8.319100E+06 | 0.00E+00 | 1 | | | | |
| 392.326216 | 1.43E-04 | 2.210743E+07 | 2.02E+07 | 4 | | | | |
| 394.138692 | 2.72E-04 | 7.325000E+06 | 1.62E+05 | 2 | | | | |

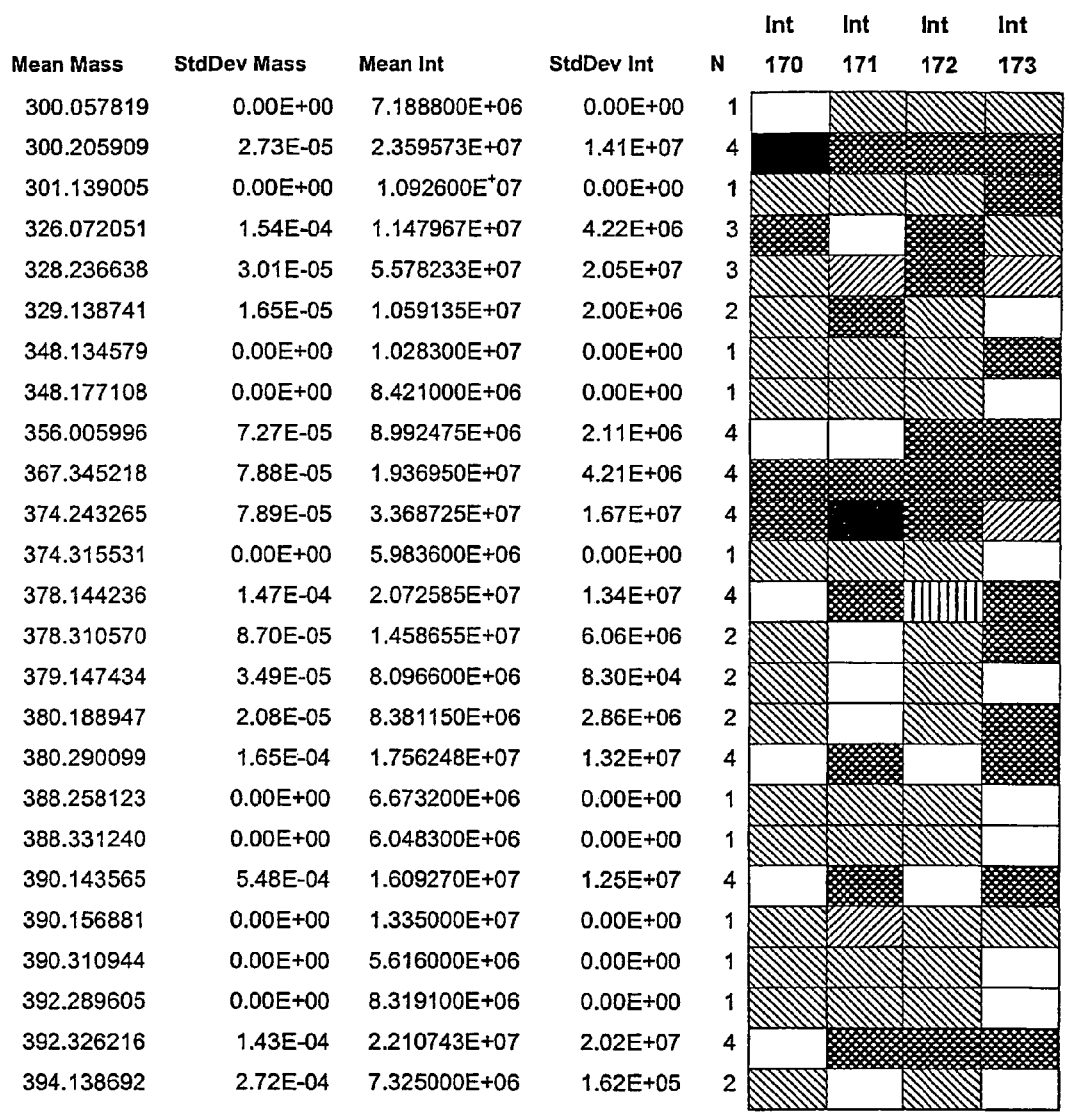

Key: (absolute intensity level)

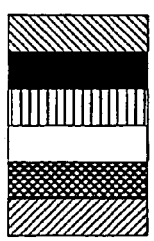

< 1.00E+06 (noise)
<=2.00E+06
<=5.00E+06
<=1.00E+07
<=5.00E+07
<=1.00E+08

Figure 5: Ratio of Intensity of Each Sample Peak to Mean Intensity
| Mean Mass | StdDev Mass | Mean Int | StdDev Int | N | Int 170 | Int 171 | Int 172 | Int 173 |
|---|---|---|---|---|---|---|---|---|
| 300.057819 | 0.00E+00 | 7.188800E+06 | 0.00E+00 | 1 | | | | |
| 300.205909 | 2.73E-05 | 2.359573E+07 | 1.41E+07 | 4 | | | | |
| 301.139005 | 0.00E+00 | 1.092600E+07 | 0.00E+00 | 1 | | | | |
| 326.072051 | 1.54E-04 | 1.147967E+07 | 4.22E+06 | 3 | | | | |
| 328.236638 | 3.01E-05 | 5.578233E+07 | 2.05E+07 | 3 | | | | |
| 329.138741 | 1.65E-05 | 1.059135E+07 | 2.00E+06 | 2 | | | | |
| 348.134579 | 0.00E+00 | 1.028300E+07 | 0.00E+00 | 1 | | | | |
| 348.177108 | 0.00E+00 | 8.421000E+06 | 0.00E+00 | 1 | | | | |
| 356.005996 | 7.27E-05 | 8.992475E+06 | 2.11E+06 | 4 | | | | |
| 367.345218 | 7.88E-05 | 1.936950E+07 | 4.21E+06 | 4 | | | | |
| 374.243265 | 7.89E-05 | 3.368725E+07 | 1.67E+07 | 4 | | | | |
| 374.315531 | 0.00E+00 | 5.983600E+06 | 0.00E+00 | 1 | | | | |
| 378.144236 | 1.47E-04 | 2.072585E+07 | 1.34E+07 | 4 | | | | |
| 378.310570 | 8.70E-05 | 1.458655E+07 | 6.06E+06 | 2 | | | | |
| 379.147434 | 3.49E-05 | 8.096600E+06 | 8.30E+04 | 2 | | | | |
| 380.188947 | 2.08E-05 | 8.381150E+06 | 2.86E+06 | 2 | | | | |
| 380.290099 | 1.65E-04 | 1.756248E+07 | 1.32E+07 | 4 | | | | |
| 388.258123 | 0.00E+00 | 6.673200E+06 | 0.00E+00 | 1 | | | | |
| 388.331240 | 0.00E+00 | 6.048300E+06 | 0.00E+00 | 1 | | | | |
| 390.143565 | 5.48E-04 | 1.609270E+07 | 1.25E+07 | 4 | | | | |
| 390.156881 | 0.00E+00 | 1.335000E+07 | 0.00E+00 | 1 | | | | |
| 390.310944 | 0.00E+00 | 5.616000E+06 | 0.00E+00 | 1 | | | | |
| 392.289605 | 0.00E+00 | 8.319100E+06 | 0.00E+00 | 1 | | | | |
| 392.326216 | 1.43E-04 | 2.210743E+07 | 2.02E+07 | 4 | | | | |
| 394.138692 | 2.72E-04 | 7.325000E+06 | 1.62E+05 | 2 | | | | |
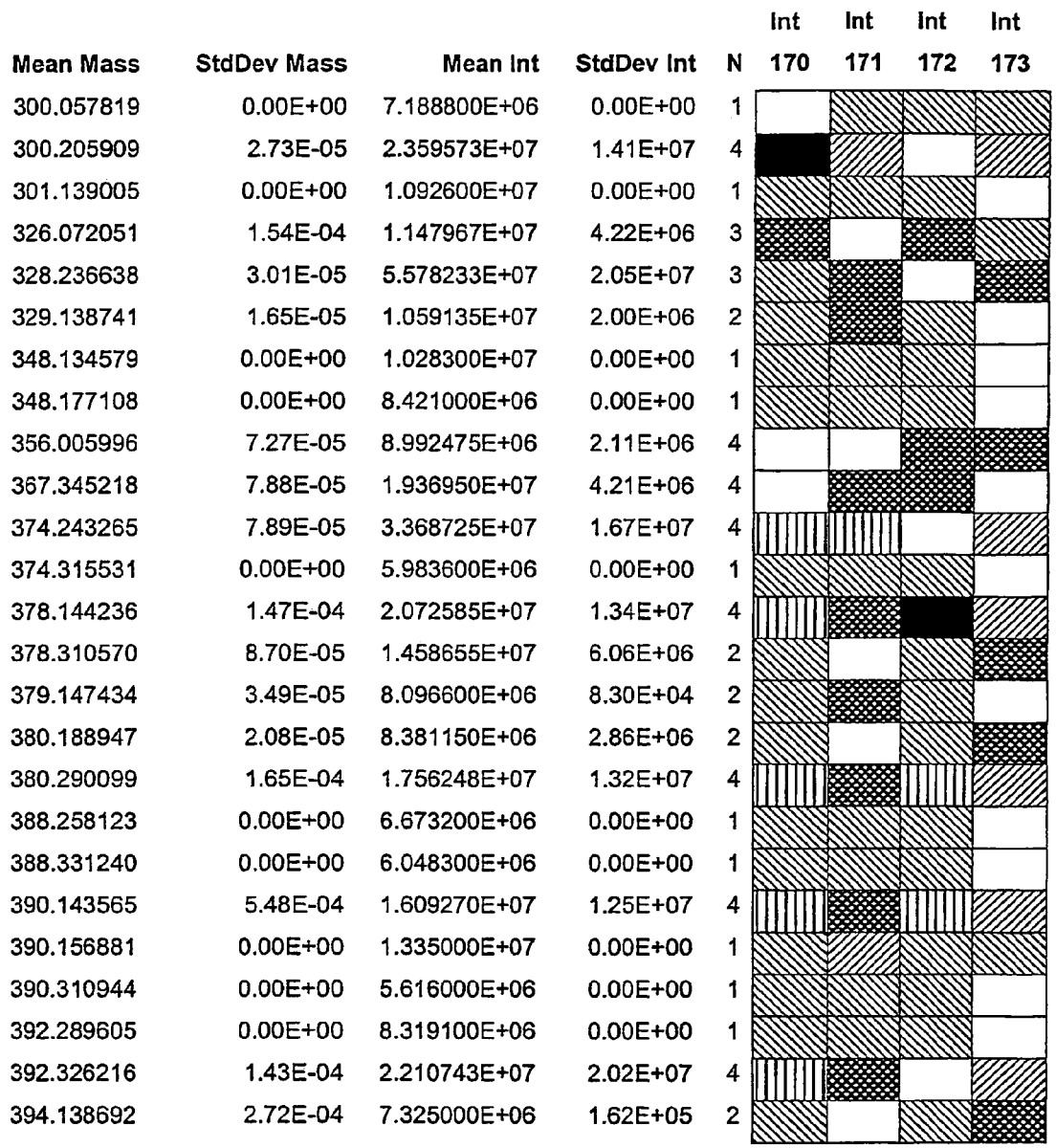
Key : (ratio * 100)
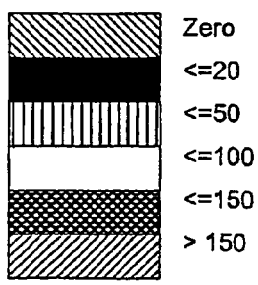
Zero
<=20
<=50
<=100
<=150
> 150

Figure 6: Ratio of Intensity of Each Sample Peak to Intensity of Sample #170
| Mean Mass | StdDev Mass | Mean Int | StdDev Int | N | Int 170 | Int 171 | Int 172 | Int 173 |
|---|---|---|---|---|---|---|---|---|
| 300.057819 | 0.00E+00 | 7.188800E+06 | 0.00E+00 | 1 | | | | |
| 300.205909 | 2.73E-05 | 2.359573E+07 | 1.41E+07 | 4 | | | | |
| 301.139005 | 0.00E+00 | 1.092600E+07 | 0.00E+00 | 1 | | | | |
| 326.072051 | 1.54E-04 | 1.147967E+07 | 4.22E+06 | 3 | | | | |
| 328.236638 | 3.01E-05 | 5.578233E+07 | 2.05E+07 | 3 | | | | |
| 329.138741 | 1.65E-05 | 1.059135E+07 | 2.00E+06 | 2 | | | | |
| 348.134579 | 0.00E+00 | 1.028300E+07 | 0.00E+00 | 1 | | | | |
| 348.177108 | 0.00E+00 | 8.421000E+06 | 0.00E+00 | 1 | | | | |
| 356.005996 | 7.27E-05 | 8.992475E+06 | 2.11E+06 | 4 | | | | |
| 367.345218 | 7.88E-05 | 1.936950E+07 | 4.21E+06 | 4 | | | | |
| 374.243265 | 7.89E-05 | 3.368725E+07 | 1.67E+07 | 4 | | | | |
| 374.315531 | 0.00E+00 | 5.983600E+06 | 0.00E+00 | 1 | | | | |
| 378.144236 | 1.47E-04 | 2.072585E+07 | 1.34E+07 | 4 | | | | |
| 378.310570 | 8.70E-05 | 1.458655E+07 | 6.06E+06 | 2 | | | | |
| 379.147434 | 3.49E-05 | 8.096600E+06 | 8.30E+04 | 2 | | | | |
| 380.188947 | 2.08E-05 | 8.381150E+06 | 2.86E+06 | 2 | | | | |
| 380.290099 | 1.65E-04 | 1.756248E+07 | 1.32E+07 | 4 | | | | |
| 388.258123 | 0.00E+00 | 6.673200E+06 | 0.00E+00 | 1 | | | | |
| 388.331240 | 0.00E+00 | 6.048300E+06 | 0.00E+00 | 1 | | | | |
| 390.143565 | 5.48E-04 | 1.609270E+07 | 1.25E+07 | 4 | | | | |
| 390.156881 | 0.00E+00 | 1.335000E+07 | 0.00E+00 | 1 | | | | |
| 390.310944 | 0.00E+00 | 5.616000E+06 | 0.00E+00 | 1 | | | | |
| 392.289605 | 0.00E+00 | 8.319100E+06 | 0.00E+00 | 1 | | | | |
| 392.326216 | 1.43E-04 | 2.210743E+07 | 2.02E+07 | 4 | | | | |
| 394.138692 | 2.72E-04 | 7.325000E+06 | 1.62E+05 | 2 | | | | |
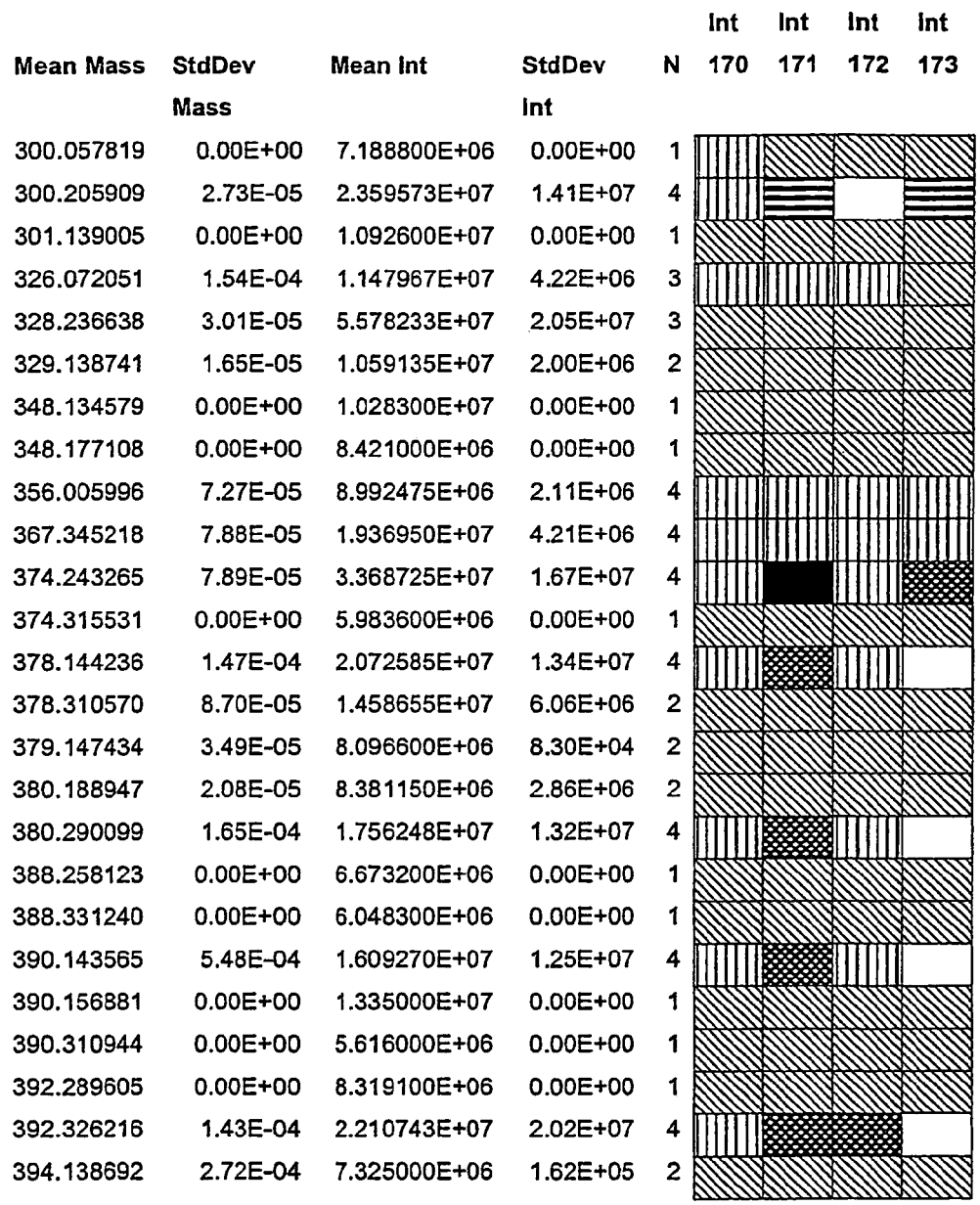
Key: (ratio * 100)
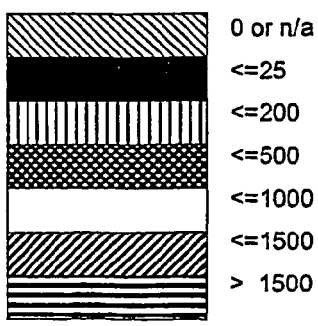
0 or n/a
<=25
<=200
<=500
<=1000
<=1500
> 1500

METHOD OF VISUALIZING NON-TARGETED METABOLOMIC DATA GENERATED FROM FOURIER TRANSFORM ION CYCLOTRON RESONANCE MASS SPECTROMETERS

The present invention relates to methods of displaying data from analytical instruments. More specifically, the present invention relates to methods of displaying data from mass spectroscopy instruments and data structures containing such data.

BACKGROUND OF THE INVENTION

Metabolite profiling is an emerging science that is used in determining gene function, effects of genetic engineering on an organism, substantive equivalence, drug mechanisms of action, adverse drug reaction monitoring and the biochemical basis of diseases. Non-targeted metabolic profiling using FT-ICR-MS identifies a large number of metabolites from complex biological extracts. The final output from such analyses is the masses and intensities of observed metabolites. The masses can be used to determine the molecular formulas, and thus the identity of the metabolites present in the sample, whereas the intensity is used to determine the amount of the metabolite present in the sample. By comparing the metabolite profiles of different biological samples, metabolite changes can be observed. These biochemical changes can then be used to understand the effect of the experimental event.

Although multiple visualization tools have been developed to display mass spectral and chromatographic data as well as databases to store, organize, and search this type of data, these tools work only for targeted analyses of known molecules. Currently, there is no effective way to display or organize information from multiple non-targeted sample analyses such that a user can quickly identify changes in metabolite profiles.

The ability to view and interpret large amounts of metabolite data is a rate-limiting step in the study of biological systems using non-targeted metabolomic methods. The creation of a process that would allow users to quickly interpret and report their findings would dramatically reduce the time and thus the cost of functional genomics utilizing non-targeted metabolomics.

There is a need in the art for novel methods of displaying data obtained by analytical instruments. Further, there is a need in the art for novel methods of displaying or visualizing data from large numbers of non-targeted samples. Also, there is a need in the art for methods and data structures to organize and display in a 2-D array format, non-targeted metabolomic data arising from FT-ICR-MS. There is also a need to link the displayed data to additional databases to characterize or analyse further the displayed data.

It is an object of the present invention to overcome disadvantages of the prior art.

The above object is met by a combination of the features of the main claims. The sub claims disclose further advantageous embodiments of the invention.

SUMMARY OF THE INVENTION

The present invention relates to methods of displaying data from analytical instruments. More specifically, the present invention relates to methods of displaying data from mass spectroscopy instruments and data structures containing such data.

According to the present invention there is provided a method of displaying spectroscopic data comprising the steps of, i) obtaining spectroscopic data from a plurality of samples, each sample comprising one or more components wherein each component is characterized by an ordered pair (X,Y) of data comprising data element value X and data element value Y, wherein X is a data element value equivalent or directly proportional to the mass of the component, and Y is a data element value equivalent or directly proportional to the amount of the component;

ii) identifying all unique components comprising a common data element value X in said samples; computing the average of all X therefrom; and determining the average and optionally the standard deviation for all Y values from all ordered data pairs comprising a common X, and;

iii) generating a data structure comprising an array of codable cells, each cell color coded or assigned an identifiable characteristic based on the relationship of the amount of each unique component present in each of said samples in relation to a predetermined value or other characteristic of the spectroscopic data.

Further, according to the present invention there is provided a method for visualizing multiple FT-ICR-MS metabolite analysis data files that contain mass and intensity values. The method comprises the following steps:

i) selecting the files that are to be visualized;

ii) combining all of the selected files together, sorting all of the metabolites according to their mass, and identifying all of the unique masses that are present in all of the selected files. The average and standard deviation of each unique mass and the average and standard deviation of the intensities observed and the number of files in which the unique mass is found is determined.

iii) creating a data structure comprising a two dimensional (2-D) array in which the unique mass list defines the vertical axis and the number of files selected defines the horizontal axis. The amount of the metabolite present is displayed in cells defined by the vertical and horizontal axis coordinates according to a user-defined color code. The user may be provided the option of viewing the data in any number of ways, for example, but not limited to, by a) observed metabolite intensity; b) the ratio or percentage of the observed intensity to the: average intensity of that metabolite from the files selected; c) the ratio or percentage of the observed intensity to the observed intensity of one of the selected files, or a combination thereof. Thus, the method allows for the rapid and condensed display or visualization of multiple metabolite data files. As a result the determination and identification of metabolite changes in complex mixtures may be greatly simplified.

Also provided by the present invention is a method for visualizing multiple FT-ICR-MS, non-targeted complex sample analyses, comprising the steps of: creating a metabolite data file consisting of mass and intensity data and/or molecular formula data and/or other identifying data such as ionization mode, chemical class, extraction mode, file name, experimental condition, etc., in either neutral or charged forms for each independent analysis, selecting and combining a number of these data files into one file; sorting the data in the combined file by mass or molecular formula to batch together all unique metabolites from the selected files; performing statistical calculations on each of the metabolite batches (including but not limited to average and standard deviation and the number of files out of the total number of files selected that the metabolite was observed in; displaying this data in any of three ways, one, using the unique mass or molecular formula as the y-axis and file name as the x-axis, fill in for each file either the observed intensity or the observed intensity as a ratio or percent of the average intensity of the metabolite observed from the selected files, or the observed intensity as a percent or ratio of the observed intensity from one of the files selected; displaying either zero or a value corresponding to the noise level or detection limit or any other such qualifier in situations in which a metabolite is not observed in one file but is in another; assigning a color code to the intensity or ratio in each of the cells defined by the x and y coordinates described above.

Also contemplated by the present invention are data structures produced by the method of the present invention as defined above. Further, the data structures may comprise a computer readable medium, hardware, software or a combination thereof permitting information to be transferred to or from the data structure.

This summary does not necessarily describe all necessary features of the invention but that the invention may also reside in a sub-combination of the described features.

BRIEF DESCRIPTION OF THE DRAWINGS

These and other features of the invention will become more apparent from the following description in which reference is made to the appended drawings wherein:

FIG. 1 is an illustration of a metabolite data file from a single analysis of a biological sample by FT-ICR-MS.

FIG. 2 is an illustration of a combined metabolite data file from multiple biological sample analyses by FT-ICR-MS.

FIG. 3 is an illustration of a combined metabolite data file generated from multiple biological sample analyses by FT-ICR-MS in which all unique masses have been identified, the average and standard deviation of each unique mass and its intensity determined and the number of files containing the particular unique mass is displayed.

FIG. 4 is an illustration of a data structure comprising an array of the combined data file in which the y-axis is comprised of the total sum of unique masses observed from all selected data files and the x-axis is defined by the file number of the selected data files. In each cell defined by these axes is displayed the corresponding metabolite intensity in a color-coded fashion.

FIG. 5 is an illustration of a data structure comprising an array of the combined data file in which the y-axis is comprised of the total sum of unique masses observed from all selected data files and the x-axis is defined by the file number of the selected data files. In each cell defined by these axes is displayed the ratio of the corresponding metabolite intensity to the average metabolite intensity in a color-coded fashion.

FIG. 6 is art illustration of a data structure comprising an array of the combined data file in which the y-axis is comprised of the total sum of unique masses observed from all selected data files and the x-axis is defined by the file number of the selected data files. In each cell defined by these axes is displayed the ratio of the corresponding metabolite intensity to the observed metabolite intensity from one of the selected data files, in a color-coded fashion.

DESCRIPTION OF PREFERRED EMBODIMENT

The present invention relates to methods of displaying data from analytical instruments. More specifically, the present invention relates to methods of displaying data from mass spectroscopy instruments and data structures containing such data.

The following description is of a preferred embodiment by way of example only and without limitation to the combination of features necessary for carrying the invention into effect.

According to an embodiment of the present invention, there is provided a method of analysing spectroscopic data comprising the steps of,
  i) obtaining spectroscopic data from a plurality of samples, each sample comprising one or more components wherein each component is characterized by at least an ordered pair (X,Y) of data comprising data element value X and data element value Y, wherein X is a data element value equivalent or directly proportional to the mass of the component, and Y is a data element value equivalent or directly proportional to the amount of the component;
  ii) identifying all unique components comprising a common data element value X in said samples; computing the average of all X therefrom; and determining the average and standard deviation for all Y values from all ordered data pairs comprising a common X;
  iii) generating a data structure comprising an array of codable cells, each cell assigned a color or other identifiable characteristic based on the relationship of the, amount of each unique component present in each of said samples in relation to a predetermined value or other characteristic of the spectroscopic data.

By the term "spectroscopic data" it is meant data from any spectroscopic instrument, for example, but not limited to visible, IR, or UV spectrometer, mass spectrometer, NMR apparatus or the like. Preferably the spectroscopic data is from a mass spectrometer.

Any mass spectrometer may be employed in the method of the present invention. Further, the mass spectrometer may be employed in combination with other analytical devices such as, but not limited to chromatographic systems. Preferably, the mass spectrometer is a Fourier transform ion cyclotron mass spectrometer. A description of a Fourier transform ion cyclotron mass spectrometer is described in CA 2,298,181 and PCT/CA01/00111 which are both herein incorporated by reference.

By the term "sample" it is meant any composition for which data may be acquired. For example, the sample may comprise any biological sample, or fraction or extract thereof. The biological sample may be unprocessed or processed by one or more steps known in the art. Examples of such steps include, but are not limited to, extraction steps, purification steps, chemical reaction steps or any combination thereof. In this regard the sample may be processed in any manner known in the art. The biological sample may also comprise other components that have been added thereto. For example, but not wishing to be limiting, the biological sample may comprise components which are commonly added to mass spectroscopy samples as would be known to those of skill in the art. In an aspect of an embodiment, the sample is a complex sample comprising a plurality of components that may be resolved or separated by a mass spectrometer.

By the term "ordered, pair (X,Y) of data" it is meant data which characterizes a component in a sample. For example, X may comprise a numerical value for the mass of a component and Y may comprise a numerical value for the amount the component. Further, X may comprise a value or other identifier which is a characteristic of the specific component. For example, but not wishing to be limiting, X may comprise the retention time in a column, a specific signal location in a mass spectrometer detector, or the like. Further, X may comprise the mass, chemical formula or a structural formula of a specific component. Further, other data such as, but not limited to, intensity, molecular formula data, ionization mode, chemical class, extraction mode, filename, experimental condition, or a combination thereof may be provided in a higher ordered data set and such data sets are fully contemplated by the present invention.

By the term "unique components" it is meant the collection of all specific components which are present in at least one sample, of all the samples analyzed.

By the term "data structure" it is meant an ordered grouping of information derived from a plurality of samples. The data structure may comprise a database or an array comprising a plurality of cells containing information derived or processed from the samples. Further the data structure may comprise a plurality of cells wherein one or more cells are assigned a color code based on a value contained in the cell. However, the cells may be assigned any other attribute or characteristic identifier based on the value contained in the cell. By other attribute or color characteristic code it is meant a color, pattern, shade, or combination thereof which may be employed to differentiate between cells based on the value contained therein.

By the term "predetermined value or other characteristic of the spectroscopic data" it is meant a value such as, but not limited to, an observed component intensity, or average intensity or standard deviation of one or more component intensities, or the ratio or percentage of an observed intensity for one or more components in relation to the average intensity for one or more other components in one or more samples. Further, other values and characteristics are contemplated by the present invention.

The color or other identifiable characteristic as described above may optionally define a range of values. For example, but not wishing to be limiting in any manner, the color red may be employed for values between A and B, while the color blue may be employed for color values between C and D. Other combinations are also possible.

In an aspect of an embodiment, there is provided a method of displaying data obtained from Fourier transform ion cyclotron resonance mass spectrometry (FT-ICR-MS) of complex multi-component biological samples. The method is described with reference to FIGS. 1-6. However, reference to the figures is meant for illustrative purposes only and is not meant to limit the invention in any manner.

Referring now to FIG. 1, there is shown data which may be obtained from a mass spectroscopy instrument. The data shown in FIG. 1 was obtained by FT-ICR-MS of a single sample ("n"=1) arbitrarily termed #170. Sample #170 comprises 10 components. Each of the components may be characterized by at least an ordered pair (X,Y) of data that is, its neutral mass (nMass (X)) and its intensity (Intensity (Y)) values. Also shown in FIG. 1 are members of elements (NE), molecular formulae, and errors (Err) associated with the formulae, and thus the ordered data may be expanded if desired, for example, but not limited to (X,Y,A,B,C) corresponding to for example, but not limited to (nMass (X), Intensity (Y), NE (A), Molecular Formula#1 (B), Err(C)). Determination of molecular formulae and errors associated therewith are easily determined by a person of skill in the art, based on the mass of a component in the sample. There are numerous algorithms known in the art for determining such formulae and any one or a combination thereof may be employed in the method of the present invention.

As will be evident to a person of skill in the art, each independent sample that is analyzed by FT-ICR-MS produces data which may be organized in a manner similar to the data shown in FIG. 1. Also, as will be evident to someone of skill in the art, individual samples may comprise one or more identical components, for example, but not limited to as determined by their nMass. These components may be present in similar amounts or dissimilar amounts. Further, individual samples may comprise different components.

Referring now to FIG. 2, there is shown mass spectroscopy data obtained for 4 independent samples arbitrarily indicated by sample #s 170, 171, 172 and 173. Each independent sample comprises a plurality of components as shown by the mass numbers and their corresponding intensities. As illustrated, independent sample #170 comprises 10 components, independent sample #171 comprises 16 components, independent sample #172 comprises 10 components and independent sample #173 comprises 22 components. Also evident by FIG. 2 is that the first component in sample#170 having mass 300.057819 and intensity 7.19×$10^6$ is a unique component that is not found in any of the other independent samples. In contrast, the second component of sample 170 characterized by mass 390.205935 and intensity 6.84×$10^6$ is also present in Sample #171, 172 and 173 as components characterized by mass values of 300.20593, 0.300.205883, and 360.205886, respectively. As will be evident to a person of skill in the art, the mass of two identical components resolved by a mass spectrometer in separate analyses may yield slightly different mass values, as shown above. However, there are various methods known in the art which may be employed to determine whether the components are the same, and such methods are fully contemplated by the present invention.

As further shown in FIG. 2, spectroscopic data from multiple samples may be combined into a single data structure and optionally sorted and processed to determine all of the unique masses that are present in all of the independent samples. Other information that may be determined includes, but is not limited to the average, standard deviation, and number of times each mass is present in the samples. Preferably, the information is tabulated in a data structure or an array as shown in FIG. 3.

FIG. 3 shows a data structure tabulating results of the mean masses (average) obtained for each unique component present in all of the samples analyzed. For example, but not to be considered limiting in any manner, mean mass 300.057819 is the mass of the first component of Sample #170 (see FIGS. 1 and 2) and comprises a mean intensity of 7.188800×$10^6$. Since the component is not found in any of the other samples, the standard deviation of its mass and standard deviation of its intensity is 0. In contrast, the mean mass shown as 300.205909 is the average mass of 4 components identified in samples 170, 171, 172 and 173 comprising individual mass values of 300.205935, 300.20593, 300.205883 and 300.205886 and corresponding intensity values of 6.84×$10^6$, 3.56×$10^7$, 1.43×$10^7$ and 3.77×$10^7$ respectively (see FIG. 2). Shown in FIG. 3 is the mean mass for all components in the independent samples, standard deviation of the mean mass, mean intensity of all components with common mass, the standard deviation of the mean intensity, the number of samples comprising a unique mass, and the intensity of each mass in its respective sample #. In the event that a particular component is not found in a specific sample #, no value is entered. For example, mean mass 300.057819 comprising mean intensity $7.188800 \times 10^6$ is found only in sample #170 and thus the remaining specific sample intensities cells are blank. Each intensity value listed in the specific sample may be assigned a color code, or other identifiable characteristic based on the magnitude of intensity value, as shown in FIG. 4.

Referring now to FIG. 4, there is shown a data structure wherein each specific intensity value listed for a specific sample number has been assigned a specific color code depending on the magnitude of the intensity value. For example, but not to be considered limiting in any manner, non-present intensity or intensity values from 0 to less than $1 \times 10^6$ are assigned a first color, while intensity values ranging from $2 \times 10^5$ to less than or equal to $2 \times 10^6$ are assigned a second color, and so on. The ranges may be adjusted as necessary and may be defined by any colors desired.

Also contemplated by the present invention, the data in the data structure may be processed further or displayed in alternate ways. For example, the intensity values for each sample number may be compared to the average intensity of the component for all independent samples for example, but not limited to as shown in FIG. 5. Alternatively, but not wishing to be considered limiting, the data may be processed to compare all of the intensities of components in a specific sample, for example, but not limited to sample #170 as shown in FIG. 6.

In an alternate embodiment of the present invention, there is provided a method for visualizing multiple FT-ICR-MS metabolite analysis data files that contain mass and intensity values. The method comprises the following steps:
i) selecting the files that are to be visualized;
ii) combining all of the selected files together, sorting all of the metabolites according to their mass, and identifying all of the unique masses that are present in all of the selected files. The average and standard deviation of each unique mass and the average and standard deviation of the intensities observed and the number of files in which the unique mass is found is determined.
iii) creating a data structure comprising a two dimensional (2-D) array in which the unique mass list defines the vertical axis and the number of files selected defines the horizontal axis. The amount of the metabolite present is displayed in cells defined by the vertical and horizontal axis coordinates according to a user-defined color code. The user may be provided the option of viewing the data in any number of ways, for example but not limited to by a) observed metabolite intensity; b) the ratio or percentage of the observed intensity to the average intensity of that metabolite from the files selected; c) the ratio or percentage of the observed intensity to the observed intensity of one of the selected files, or a combination thereof. Thus, the method allows for the rapid and condensed display or visualization of multiple metabolite data files. As a result, the determination and identification of metabolite changes in complex mixtures may be greatly simplified.

The present invention further contemplates any of the above mentioned data structures. Further, the present invention contemplates any of the above mentioned data structures on a computer readable medium, for example, but not limited to a compact disc, floppy disc, hard drive or the like, as will be understood by a person of skill in the art.

Also contemplated by the present invention is the data structure of the present invention in combination with necessary hardware, software, or a combination thereof which permits the data structure of the present invention to obtain data from or pass data to one or more other databases, for example, but not limited to natural product databases, metabolic pathway databases, bioinformatics programs or a combination thereof. Further the cells of the data structure can be linked to one or more databases containing all the experimental information regarding the metabolite including, but not limited to the file name, observed mass, observed intensity, quality assurance control data, such as, but not limited to, internal standard data, molecular formulas and mass errors.

In an alternate embodiment, the present invention provides a method as defined above wherein the ordered pair of data is derived from a higher ordered data set $(A_1 \ldots A_n, X, Y, B_1 \ldots B_n)$.

The present invention also: provides a method as defined above wherein the predetermined value or other characteristic of the data is selected from the group consisting of:
a) observed metabolite intensity;
b) the ratio or percentage of the observed intensity to the average intensity of that metabolite from the files selected;
c) the ratio or percentage of the observed intensity to the observed intensity of one or more of the selected files;
or a combination thereof. However, any other characteristic of the data set may be employed in the method, as would be known to a person of skill in the art.

The present invention also contemplates a system for analysing spectroscopic data comprising a computer processing unit, the processing unit capable of:
a) receiving spectroscopic data obtained from one or more samples, each sample comprising one or more components wherein each component is characterized by at least an ordered pair of data (X,Y) comprising data element X and data element Y, wherein X is a name or identifier of X, or a value equivalent or directly proportional to the mass of component X, and Y is a data element value equivalent or directly proportional to the amount of the component;
b) processing the data by identifying all unique components comprising a common data element X in the samples and optionally computing the average of all X therefrom; and determining the average and optionally the standard deviation for all Y values from ordered data pairs comprising a common data element X; and
iii) generating a data structure comprising an array, the array comprising a plurality of codable cells, each cell representing a unique component in a sample and assigned a color or other identifiable characteristic based on a relationship to a characteristic of the data, an extrinsic value or a value set by a user.

The system may further include a monitor to display the data structure, a spectroscopic instrument to generate the spectroscopic data, or both. Further, any relationship to a characteristic of the data may be employed, as would be understood by a person of skill in the art, for example, but not limited to
a) the average or median of all Y values in one or more ordered data sets;
b) the average or median of all Y values with unique data element X;
c) an extrinsic value obtained from a program, database or the like; or
d) a value input by a user.

Thus, the method of the present invention provides a means to analyze, display, visualize and process large amounts of data from complex samples, such as but not limited to, biological samples and extracts. Further, the method provides a means to analyze the information in a non-targeted and unbiased fashion to determine the differences between samples.

The above description is not intended to limit the claimed invention in any manner, Furthermore, the discussed combination of features might not be absolutely necessary for the inventive solution.

The present invention will be further illustrated in the following examples. However, it is to be understood that these examples are for illustrative purposes only, and should not be used to limit the scope of the present invention in any manner.

EXAMPLES

Example 1

Analysis of Multiple Non-targeted Samples

Processed data files from complex samples are first analyzed as described in a previous patent application (No. 2,298,181, Canada, No. PCT/CA01/00111). The results of this analysis are in the format as shown in FIG. 1. Data from multiple files are then combined together as shown in FIG. 2. At this stage the data is reduced such that only file name, ionization/extraction code, mass and intensity values remain. This combined file is then processed to determine all of the unique masses. The average, standard deviation, and number of each unique mass is then determined. This list represents the y-axis. A column is created for each file that was originally selected to be analyzed. This list represents the x-axis. The intensity for each mass found in each of the files selected is then filled into its representative x,y coordinate as is shown in FIG. 3. Coordinates that do not contain an intensity are left blank. Once in the array, the data can be further processed and visualized by using color codes. Three such possibilities are shown. As shown in FIG. 4 a user may visualize data by intensity values using color codes without any additional processing; As shown in FIG. 5 a user may further process the data (relative to FIG. 4) by comparing the intensity to the average intensity of that metabolite from all samples selected; and in FIG. 6 the user may further process the data (relative to FIG. 4) to compare all of the intensities to a specific file (in this case file 170). Thus, the user can simultaneously display and interpret multiple files. An important consideration is that this method may comprise, but is not limited to a self-creating array. The final x and y axes are may not be determined prior to the creation of the, array but during its creation.

All references are herein incorporated by reference.

The present invention has been described with regard to preferred embodiments. However, it will be obvious to persons skilled in the art that a number of variations and modifications can be made without departing from the scope of the invention as described herein.

The embodiments of the invention in which an exclusive property of privilege is claimed are defined as follows:

1. A computer implemented method of performing non-targeted analysis on data collected on a plurality of detected components from a plurality of samples, to identify components of interest, comprising the steps of:
   a) building a database of said data collected on a plurality of detected components from a plurality of samples, wherein each data record for each of said detected components from each of said samples includes a first spectrographic data characteristic of said component and a second spectrographic data characteristic of the amount of said component;
   b) generating an ordered pair (X, Y) of data for each of the components contained in said database where X is correlated with said first spectrographic data and Y is correlated with said second spectrographic data;
   c) associating each of said ordered pairs (X, Y) with one or more secondary data elements of identifying data;
   d) comparing all of said data elements X contained in the database and determining which data elements X are substantially the same;
   e) from said data elements X which were so determined to be substantially the same, calculating the average value of data element X for each such data element X;
   f) from data elements X which were not determined to be substantially the same, calculating the average value of data element X for each such data element X;
   g) generating a two dimensional array of said data wherein one axis is defined by a plurality of said averaged data elements X so determined in steps (e) and (f) and the other axis is defined by at least one secondary data element, and each array cell described by the intersection of such axes contains data specific to one or both of the axes so defined and selected from the group consisting of: data element X, data element Y, and secondary data elements of identifying data; and
   h) comparing elements of said two dimensional array to identify differences between said samples, said differences identifying components of interest.

2. The method as defined in claim 1, wherein said step of comparing elements further comprises the step of comparing elements of said two dimensional array to identify similarities between said samples.

3. The method as defined in claim 1, wherein said step of generating comprises the step of generating said two dimensional array of said data wherein one axis is defined by a plurality of said averaged data elements X so determined in steps (e) and (f) and the other axis is defined by at least two secondary data elements.

4. The method as defined in claim 1, wherein said component data of step (a) comprises peak picked data representing peaks extrapolated from raw spectroscopic data.

5. The method as defined in claim 1, further comprising the step of outputting said two dimensional array of said data in a two dimensional display, thereby offering a visual representation of said data.

6. The method as defined in claim 1, wherein the components are metabolites.

7. The method as defined in claim 1, wherein the samples are biological samples.

8. The method as defined in claim 1, wherein the first and second spectroscopic data are derived from a Fourier transform ion cyclotron resonance mass spectrometer (FTMS).

9. The method as defined in claim 1, wherein the first and second spectroscopic data are derived from an analytical instrument selected from the group consisting of: mass spectrometer, visible, IR, or UV spectrometer, NMR (Nuclear Magnetic Resonance).

10. The method as defined in claim 1, wherein the first and second spectroscopic data are derived from the combination of a mass spectrometer and a chromatographic system.

11. The method as defined in claim 1, wherein the spectrographic data comprising X is the mass of the component.

12. The method as defined in claim 1, wherein the spectrographic data comprising X is the combination of the mass and retention time of the component.

13. The method as defined in claim 1, wherein the spectrographic data comprising Y is the intensity of the component.

14. The method as defined in claim 1, wherein the secondary data element is one or a combination of two or more elements selected from the group consisting of: file name of the sample; extraction conditions of the sample; experimental conditions from which the sample was obtained; ionization mode of the mass spectrometer; retention time of the component in a column; molecular formula of the component; mass of the component; quality assurance information regarding the sample; and quality control information regarding the sample.

15. The method as defined in claim 1, wherein data element X is the combination of the mass of the component and one or more secondary data elements selected from the group consisting of: extraction conditions of the sample; ionization mode of the mass spectrometer; and retention time of the component in a column.

16. The method as defined in claim 1, wherein the two dimensional array is organized to allow expansion along the axis defined by one or a combination of two or more secondary elements so defined as comparisons between samples are made.

17. The method as defined in claim 1, wherein the two dimensional array is organized to permit for sorting, and displaying of the data defined by Y in ascending or descending order.

18. The method as defined in claim 1, wherein the two dimensional array is organized to permit for sorting, and displaying of the data according to the mass of the components.

19. The method as defined in claim 1, wherein the two dimensional array is organized to permit for sorting, and displaying of the data according to the chromatographic retention time of the component.

20. The method as defined in claim 1, wherein the two dimensional array is organized to permit for sorting, and displaying of the data according to any combination of primary and secondary data elements, wherein the secondary elements are selected from the group consisting of: file name of the sample; extraction conditions of the sample; experimental conditions from which the sample was obtained; ionization mode of the mass spectrometer; retention time of the component in a column; molecular formula of the component, mass of the component; quality assurance information regarding the sample; and quality control information regarding the sample.

21. The method as defined in claim 1, wherein data contained within the two dimensional array defined in step (g) is passed to and further processed by a bioinformatics program.

22. The method as defined in claim 1, wherein data contained within the two dimensional array defined in step (g) is passed to a natural products database.

23. The method as defined in claim 1, wherein data contained within the two dimensional array defined in step (g) is passed to a metabolic pathway database.

24. A memory for storing data for access by an application program being executed on a data processing system, comprising a data structure stored in said memory, said data structure including information resident in a database used by said application program, said data structure comprising a two dimensional representation of spectrographic data collected from a plurality of samples, each of which contains a plurality of components, and including:

i) said spectroscopic data collected from said plurality of samples, wherein the spectroscopic data from each of said plurality of components detected in each of said samples is comprised of a first spectrographic data characteristic of said components and a second spectrographic data characteristic of the amount of said components detected in each of said samples;

j) an ordered pair (X, Y) of data for each of the components contained in the database where X is correlated with said first spectrographic data and Y is correlated with said second spectrographic data, said ordered pairs (X, Y) being associated with one or more secondary data elements of identifying data; and k) a two dimensional array of said data wherein one axis is defined by a plurality of average data elements X determined by performing the steps of:

i) comparing all said data elements X contained in the database and determining which data elements X are substantially the same;

ii) calculating the average data element X for each data element X for which a plurality of data elements X were so determined to be substantially the same; and iii) calculating the average data element X for each of the data elements X for which a plurality of data elements X were not determined to be substantially the same;

l) and the other axis is defined by one or a combination of two or more secondary data elements, and each array cell described by the intersection of such axes contains data specific to one or both of the axes so defined and selected from the group consisting of: data element X, data element Y, and secondary data elements of identifying data.

25. The memory as defined in claim 24, wherein the samples are biological samples.

26. The memory as defined in claim 24, wherein the spectroscopic data is derived from a Fourier transform ion cyclotron resonance mass spectrometer (FTMS).

27. The memory as defined in claim 24, wherein the spectroscopic data is derived from an analytical instrument selected from the group consisting of: mass spectrometer, visible, IR, or UV spectrometer, NMR (Nuclear Magnetic Resonance).

28. The memory as defined in claim 24, wherein the spectroscopic data is derived from the combination of a mass spectrometer and a chromatographic system.

29. The memory as defined in claim 24, wherein the spectrographic data comprising X is the mass of the component.

30. The memory as defined in claim 24, wherein the spectrographic data comprising X is the combination of the mass and retention time of the component.

31. The memory as defined in claim 24, wherein the spectrographic data comprising Y is the intensity of the component.

32. The memory as defined in claim 24, wherein the secondary data element is one or a combination of two or more elements selected from the group consisting of: file name of the sample; extraction conditions of the sample; experimental conditions from which the sample was obtained; ionization mode of the mass spectrometer; retention time of the component in a column; molecular formula of the component; mass of the component; quality assurance information regarding the sample; and quality control information regarding the sample.

33. The memory as defined in claim 24, wherein data element X is the combination of the mass of the component and one or more secondary data elements selected from the group consisting of: extraction conditions of the sample; ionization mode of the mass spectrometer; and retention time of the component in a column.

34. The memory as defined in claim 24, wherein the data structure is organized to allow expansion along the axis defined by one or a combination of two or more secondary elements so defined as comparisons between samples are made.

35. The memory as defined in claim 24, wherein the data structure is organized to permit for sorting, and displaying of the data defined by Y in ascending or descending order.

36. The memory as defined in claim 24, wherein the data structure is organized to permit for sorting, and displaying of the data according to the mass of the components.

37. The memory as defined in claim 24, wherein the data structure is organized to permit for sorting, and displaying of the data according to a chromatographic retention time of the component.

38. The memory as defined in claim 24, wherein the data structure is organized to permit for sorting, and displaying of the data according to any combination of primary and secondary data elements, wherein the secondary elements are selected from the group consisting of: file name of the sample; extraction conditions of the sample; experimental conditions from which the sample was obtained; ionization mode of the mass spectrometer; retention time of the component in a column; molecular formula of the component, mass of the component; and quality assurance or quality control information regarding the sample.

39. A system for performing non-targeted analysis on data collected on a plurality of detected components from a plurality of samples, to identify components of interest, comprising:
  m) means for building a database of said data collected on a plurality of detected components from a plurality of samples, wherein each data record for each of said detected components from each of said samples includes a first spectrographic data characteristic of said component and a second spectrographic data characteristic of said component;
  n) means for generating an ordered pair (X, Y) of data for each of the components contained in said database where X is correlated with said first spectrographic data and Y is correlated with said second spectrographic data;
  o) means for associating each of said ordered pairs (X, Y) with one or more secondary data elements of identifying data;
  p) means for comparing all of said data elements X contained in the database and determining which data elements X are substantially the same;
  q) means for, from said data elements X which were so determined to be substantially the same, calculating the average value of data element X for each such data element X;
  r) means for, from data elements X which were not determined to be substantially the same, calculating the average value of data element X for each such data element X; s) means for generating a two dimensional array of said data wherein one axis is defined by a plurality of said averaged data elements X so determined in steps (e) and (f) and the other axis is defined by at least one secondary data element, and each array cell described by the intersection of such axes contains data specific to one or both of the axes so defined and selected from the group consisting of: data element X, data element Y, and secondary data elements of identifying data; and
  t) means for comparing elements of said two dimensional array to identify differences between said samples, said differences identifying components of interest.

40. The system as defined in claim 39, wherein said means for comparing elements further comprises means for comparing elements of said two dimensional array to identify similarities between said samples.

41. The system as defined in claim 39, wherein said means for generating comprises means for generating said two dimensional array of said data wherein one axis is defined by a plurality of said averaged data elements X so determined by means (e) and (f) and the other axis is defined by at least two secondary data elements.

42. The system as defined in claim 39, wherein said component data of means (a) comprises peak picked data representing peaks extrapolated from raw spectroscopic data.

43. The system as defined in claim 39, further comprising means for outputting said two dimensional array of said data in a two dimensional display, thereby offering a visual representation of said data.

44. The system as defined in claim 39, wherein the components are metabolites.

45. The system as defined in claim 39, wherein the samples are biological samples.

46. The system as defined in claim 39, wherein the first and second spectroscopic data are derived from a Fourier transform ion cyclotron resonance mass spectrometer (FTMS).

47. The system as defined in claim 39, wherein the first and second spectroscopic data are derived from an analytical instrument selected from the group consisting of: mass spectrometer, visible, IR, or UV spectrometer, NMR (Nuclear Magnetic Resonance).

48. The system as defined in claim 39, wherein the first and second spectroscopic data are derived from the combination of a mass spectrometer and a chromatographic system.

49. The system as defined in claim 39, wherein the spectrographic data comprising X is the mass of the component.

50. The system as defined in claim 39, wherein the spectrographic data comprising X is the combination of the mass and retention time of the component.

51. The system as defined in claim 39, wherein the spectrographic data comprising Y is the intensity of the component.

52. The system as defined in claim 39, wherein the secondary data element is one or a combination of two or more elements selected from the group consisting of: file name of the sample; extraction conditions of the sample; experimental conditions from which the sample was obtained; ionization mode of the mass spectrometer; retention time of the component in a column; molecular formula of the component; mass of the component; quality assurance information regarding the sample; and quality control information regarding the sample.

53. The system as defined in claim 39, wherein data element X is the combination of the mass of the component and one or more secondary data elements selected from the group consisting of: extraction conditions of the sample; ionization mode of the mass spectrometer; and retention time of the component in a column.

54. The system as defined in claim 39, wherein the two dimensional array is organized to allow expansion along the axis defined by one or a combination of two or more secondary elements so defined as comparisons between samples are made.

55. The system as defined in claim 39, wherein the two dimensional array is organized to permit for sorting, and displaying of the data defined by Y in ascending or descending order.

56. The system as defined in claim 39, wherein the two dimensional array is organized to permit for sorting, and displaying of the data according to the mass of the components.

57. The system as defined in claim 39, wherein the two dimensional array is organized to permit for sorting, and displaying of the data according to the chromatographic retention time of the component.

58. The system as defined in claim 39, wherein the two dimensional array is organized to permit for sorting, and displaying of the data according to any combination of primary and secondary data elements, wherein the secondary elements are selected from the group consisting of: file name of the sample; extraction conditions of the sample; experimental conditions from which the sample was obtained; ionization mode of the mass spectrometer; retention time of the component in a column; molecular formula of the component, mass of the component; quality assurance information regarding the sample; and quality control information regarding the sample.

59. The system as defined in claim 39 wherein data contained within the two dimensional array defined by means (g) is passed to and further processed by a bioinformatics program.

60. The system as defined in claim 39 wherein data contained within the two dimensional array defined by means (g) is passed to a natural products database.

61. The system as defined in claim 39 wherein data contained within the two dimensional array defined by means (g) is passed to a metabolic pathway database.

* * * * *

UNITED STATES PATENT AND TRADEMARK OFFICE
CERTIFICATE OF CORRECTION

PATENT NO. : 7,348,143 B2
APPLICATION NO. : 10/508179
DATED : March 25, 2008
INVENTOR(S) : Douglas Heath et al.

Page 1 of 1

It is certified that error appears in the above-identified patent and that said Letters Patent is hereby corrected as shown below:

On the Title Page

Item (73) Assignee: "Phenmenome" Discoveries Inc. should be --Phenomenome-- Discoveries Inc.

Signed and Sealed this

Fifth Day of August, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,348,143 B2 | Page 1 of 1 |
| APPLICATION NO. | : 10/508179 | |
| DATED | : March 25, 2008 | |
| INVENTOR(S) | : Douglas Heath et al. | |

It is certified that error appears in the above-identified patent and that said Letters Patent is hereby corrected as shown below:

Title Pg. Item (57) Abstract:

Line 3 – "in" should be --the--

In the Specification

Col. 3, line 60 – "art" should be --an--
Col. 4, line 32 – the comma should be removed
Col. 6, line 27 – "390.205935" should be --300.205935--
Col. 6, line 30 – "0.300.205883" should be --300.205883--
Col. 6, line 30 – "360.205886" should be --300.205886--
Col. 9, line 49 – the comma should be removed

In the Claims

Claim 24 – elements listed as i), j), k) and l) in column 12, lines 3 through 29 should be a), b), c) and d) respectively.

Claim 39 – elements identified as m) through t) in column 13, lines 37 through column 14, line 5, should be a) through h) respectively. Element s) as corrected to g) should begin as a new paragraph.

Signed and Sealed this

Thirtieth Day of September, 2008

JON W. DUDAS
*Director of the United States Patent and Trademark Office*